US008646487B2

(12) United States Patent
Thompson et al.

(10) Patent No.: US 8,646,487 B2
(45) Date of Patent: Feb. 11, 2014

(54) CORROSION COUPON HOLDER

(75) Inventors: Kenneth O. Thompson, Ravenswood, WV (US); Glenn D. Rinehart, West Charleston, WV (US)

(73) Assignee: Mustang Sampling LLC, Ravenswood, WV (US)

( * ) Notice: Subject to any disclaimer, the term of this patent is extended or adjusted under 35 U.S.C. 154(b) by 704 days.

(21) Appl. No.: 12/901,726

(22) Filed: Oct. 11, 2010

(65) Prior Publication Data

US 2012/0085452 A1 Apr. 12, 2012

(51) Int. Cl.
  *F16L 55/10* (2006.01)
(52) U.S. Cl.
  USPC ............... 138/94; 138/94.3; 138/103; 73/86
(58) Field of Classification Search
  USPC ............. 138/94, 94.3, 103, 177, 178; 73/86
  See application file for complete search history.

(56) References Cited

U.S. PATENT DOCUMENTS

| | | | |
|---|---|---|---|
| 4,120,313 A | | 10/1978 | Lewis |
| 4,152,936 A | | 5/1979 | Boykin et al. |
| 4,177,676 A | | 12/1979 | Welker |
| 4,179,920 A | * | 12/1979 | Schuller et al. ............ 73/86 |
| 4,295,092 A | * | 10/1981 | Okamura ............... 324/671 |
| 4,309,899 A | * | 1/1982 | Torres ...................... 73/86 |
| 4,346,611 A | | 8/1982 | Welker |
| 4,387,592 A | | 6/1983 | Welker |
| 4,631,967 A | | 12/1986 | Welker |
| 4,697,465 A | | 10/1987 | Evans et al. |
| 5,085,250 A | | 2/1992 | Kendrick |
| 5,181,542 A | | 1/1993 | Wass et al. |
| 7,096,721 B2 | | 8/2006 | Bennett |
| D684,201 S | * | 6/2013 | Thompson et al. ......... D15/140 |

OTHER PUBLICATIONS

Orifice Fittings for "14.3", Daniel Measurement and Control, 1998.

* cited by examiner

*Primary Examiner* — Patrick F Brinson
(74) *Attorney, Agent, or Firm* — Cahn & Samuels, LLP

(57) ABSTRACT

An embodiment of the invention provides an insert for an orifice fitting in a pipeline. The insert includes a retaining member having an exteriorly facing surface dimensionally corresponding to cross-sectional interior dimensions of a carrier in the orifice fitting. Thus, the insert is positionally stabilized in a predetermined position within the pipeline and in substantial registry with the orifice fitting. A lug is affixed to the interiorly facing surface of the retaining member. The lug projects inwards towards a center of the retaining member and provides an interiorly facing mounting surface. A dielectric insulating layer is on the interiorly facing mounting surface of the lug, wherein the dielectric insulating layer includes a first element of a cooperating attachment member. The cooperating attachment member removably securely retains a corrosion coupon on the dielectric insulating layer upon engagement of the first element with a second element of the cooperating attachment member.

20 Claims, 3 Drawing Sheets

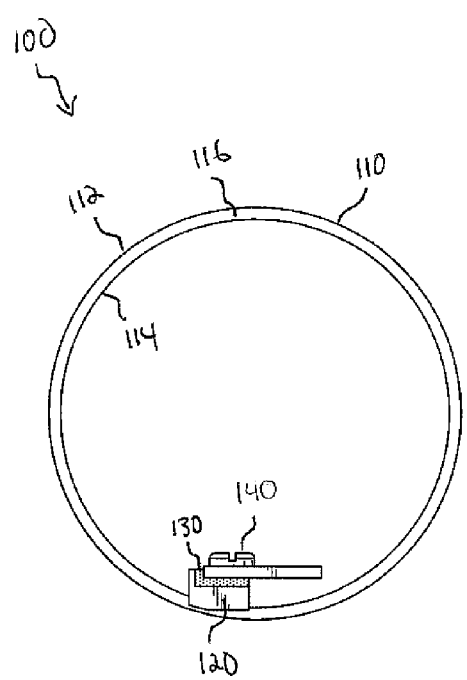
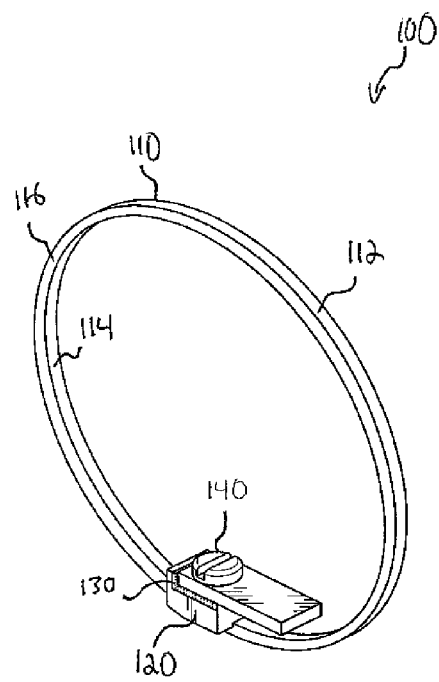
FIG. 1
FIG. 2
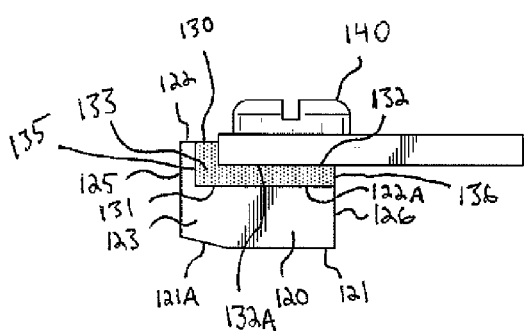
FIG. 4
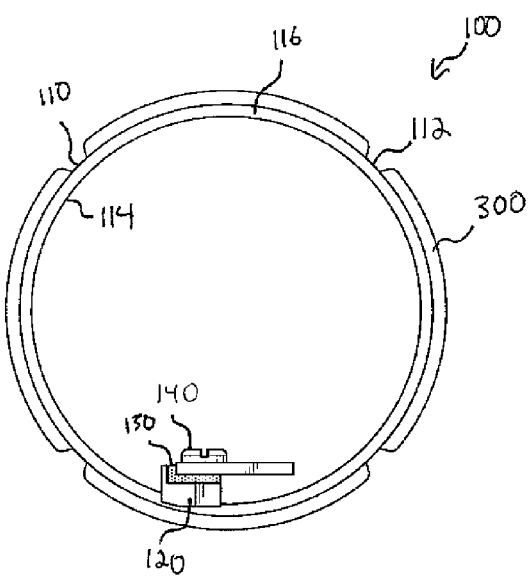
FIG. 3

CORROSION COUPON HOLDER

I. DESCRIPTION OF THE TECHNICAL FIELD

This invention relates to an improvement in measuring devices for estimating the degree of corrosion in fluid pipelines and more particularly to a novel corrosion coupon holder capable of retrofitting with and/or being utilized with existing pipeline installations.

II. BACKGROUND OF THE INVENTION

Pipelines are used to transport fluids, such as oil and gas, to and from wells, refineries, and distributions centers. In order to maintain the structural integrity of a pipeline, physical properties within the pipeline are routinely tested, such as for example, fluid pressure, fluid flow rate, and corrosion/wear of the pipeline.

The technology for construction and operation of fluid transport pipelines has advanced significantly over the past several decades. For example, it is common practice to insert so-called "orifice fittings" at periodic intervals along a pipeline. Orifice fittings are described, for example, in U.S. Pat. Nos. 5,085,250 and 5,181,542, and are used to measure fluid pressure and flow rate. Typically, such orifice fittings are installed between two sections of pipe and feature a plate carrier that retains a removable orifice plate within a stream of flowing fluid within the pipeline. Orifice plates are typically in the form of disks that are dimensioned to fit within the plate carriers. The disks include a fluid aperture or opening that is smaller than the diameter of the pipeline. By measuring the fluid pressure upstream and downstream from the orifice plate, and calculating the difference between the upstream and downstream pressures, the rate of flow in the pipeline can be estimated.

In addition to testing for fluid pressure and flow rate, pipelines are often inspected for corrosion. Fluids carried by pipelines are often corrosive. As such, corrosion within a pipeline typically occurs from the inside out. Because it is difficult to examine the interior of a pipeline, corrosion coupons are inserted into the pipeline to estimate the amount of wear. After a predetermined amount of time, the corrosion coupons are removed from the pipeline and analyzed. By determining the degree of corrosion of the coupons, the degree of corrosion of the pipeline is estimated.

Coupon holders for inserting and removing corrosion coupons from a pipeline are described, for example, in U.S. Pat. Nos. 4,120,313 and 4,697,465. Typically, such coupon holders are large cylindrical housings that are mounted over small openings in the upper wall of the pipeline. In order to install a coupon holder, an appropriately sized opening must be located along the pipeline that corresponds to the particular coupon holder to be installed. Once an opening is located, the flow of fluid within the pipeline must be shut down in order to relieve the pressure within the pipeline so that the opening can be unplugged. Therefore, in addition to the difficulties associated with locating a suitable opening, installation of additional equipment requires that the pipeline be shut down, which is often impractical or a costly interruption.

Notwithstanding the common place nature of orifice fittings in gas pipelines and the regularity of corrosion testing using coupons, the two technologies have escaped combination. There still exists a need in the art for a device for testing corrosion in a pipeline that can be quickly and easily inserted and removed from the pipeline with minimal labor and minimal cost. While prior art coupon holders possess the ability to retain a corrosion coupon in the flow of fluid within a pipeline, the use of such coupon holders involves the arduous and time-consuming task of installing new equipment, potentially at multiple locations along the pipeline.

III. SUMMARY OF THE INVENTION

The invention relates to a corrosion coupon holder having a novel structure.

It is an object of the invention to provide a structure that retrofits with and can be utilized with existing pipeline installations.

It is another object of the invention to provide a mountable and demountable structure for positionally securing a corrosion coupon within a pipeline and maintaining separation of the corrosion coupon from the pipeline wall with minimal interference with fluid flow, minimal labor, minimal complexity, and minimal cost.

It is still another object of the invention to provide a structure that is easily and quickly installed and removed from the pipeline, thereby minimizing interruption of the flow of fluid.

It is yet another object of the invention to provide a structure for estimating the degree of corrosion within a pipeline without having to physically disassemble portions of the pipeline or otherwise physically inspect the interior of the pipeline.

Specifically, it is an object of the invention to provide a structure for retaining a corrosion coupon within a stream of flowing fluid within the pipeline to expose the corrosion coupon to elements within the pipeline.

It is still yet another object of the invention to provide a structure that is durable and reusable.

Certain of these and other objects are satisfied by a device for retaining a coupon within a pipeline. The device is an insert for an orifice fitting, wherein the orifice fitting includes a carrier having select cross-sectional interior dimensions corresponding to cross-sectional interior dimensions of the pipeline. For instance, in at least one embodiment, the cross-sectional interior dimensions of the carrier (e.g., the circumference of the aperture of the carrier) are equal to or larger than the cross-sectional interior dimensions of the pipeline (e.g., the circumference of the inner wall of the pipeline).

The insert includes a retaining member having an exteriorly facing surface and an interiorly facing surface. The exteriorly facing surface dimensionally corresponds to the select cross-sectional interior dimensions of the carrier to positionally stabilize the insert in a predetermined position within the pipeline and in substantial registry with the orifice fitting.

A lug is affixed to the interiorly facing surface of the retaining member, wherein the lug projects inwards respective to the retaining member. The lug provides an interiorly facing mounting surface. The lug is positioned between the retaining member and a dielectric insulated layer.

The dielectric insulating layer is formed integrally with and on the interiorly facing mounting surface of the lug. The dielectric insulating layer includes a first element of a cooperating attachment member. The cooperating attachment member removably securely retains a corrosion coupon on the dielectric insulating layer upon engagement of the first element with a second element.

In at least one embodiment, the first element of the cooperating attachment member is an aperture or a threaded channel; and, the second element of the cooperating attachment member is an elongated member of a screw formed from non-reactive material. Further, the coupon includes an aperture and the lug includes a threaded channel for receiving the second element of the cooperating attachment member.

In at least one embodiment of the invention, the insert further includes at least one spacer having an interiorly facing surface and an exteriorly facing surface. The interiorly facing surface of the spacer engages the exteriorly facing surface of the retaining member; and, the exteriorly facing surface of the spacer engages an interiorly facing surface of the carrier.

The device is able to be retrofitted with and can be utilized with existing pipeline installations, thereby avoiding the need to install additional equipment in order to access the interior of the pipeline. For example, in one embodiment of the invention, the device is dimensioned to be securely held within a Daniel® plate carrier, available from Emerson Process Management®, Houston, Tex., United States.

The following definitions are provided to assist in understanding the scope of the invention as described herein.

"Pipe" is used to describe a conduit, channel, tube, duct, or hollow cylindrical member.

A "pipeline" is a collection of two or more pipes connected in an end-to-end fashion.

"Corrosion" means wear, degeneration, deterioration, decay, rust, oxidation, and/or erosion.

"Forming" means manufacturing by laying down, coating, molding, making, creating, constructing, assembling, producing, building, and/or developing.

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used in this application the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

In the following description, reference is made to the accompanying drawing, and which is shown by way of illustration to a specific embodiment in which the invention may be practiced. The following illustrated embodiment should make apparent an enable those skilled in the art to practice the invention. It is to be understood that other embodiment may be utilized and that structural changes based on presently known structural and/or functional equivalents may be made without departing from the scope of the invention.

Given the following detailed description, it should become apparent to the person having ordinary skill in the art that the invention herein.

IV. BRIEF DESCRIPTION OF THE DRAWING

FIG. 1 is a front view of a corrosion coupon holder according to an embodiment of the invention.

FIG. 2 is a top perspective view of a corrosion coupon holder according to an embodiment of the invention.

FIG. 3 is a front view of a corrosion coupon holder having a spacer according to an embodiment of the invention.

FIG. 4 is a front view of a hub, seat, fastener, coupon combination according to an embodiment of the invention.

V. DETAILED DESCRIPTION OF THE EMBODIMENTS

Figure 5:
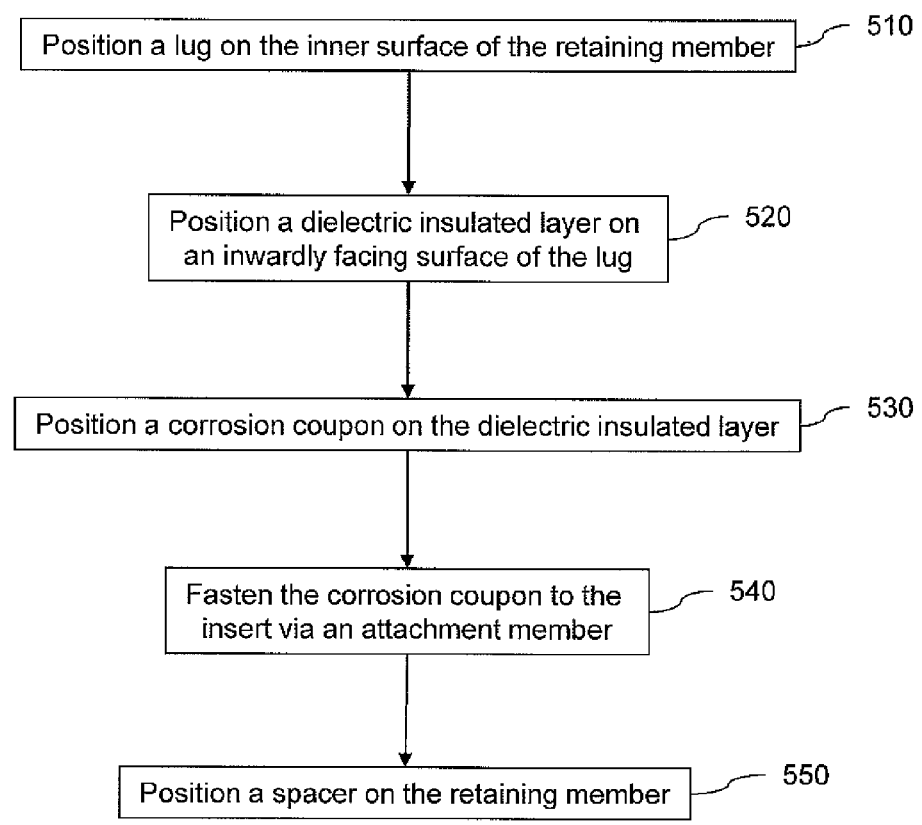
FIG. 5 is a flow diagram of a method of forming an insert for an orifice fitting according to an embodiment of the invention.

Referring now to the figures, wherein like reference numbers denote like components, elements, or features through the various illustrated embodiments discussed in detail below, the invention is a corrosion coupon holder (also referred to herein as a "device" or an "insert"). While specific implementations of the disclosed technology are discussed, it should be understood that this is done for illustration purposes only. A person skilled in the relevant art will recognize that other components and configurations may be used without departing from the spirit and scope of the invention.

FIGS. 1-2 illustrate a device 100 (also referred to herein as an "insert") for retaining a corrosion measurement device C within a pipeline P according to an embodiment of the invention. The pipeline P is a conduit for carrying pressurized fluid, such as, for example, an oil or gas pipeline. The corrosion measurement device C is a test coupon that is inserted into and retrieved from within the pipeline P to test for corrosion of the pipeline P due to the internal flow of a medium, such as a corrosive fluid.

The device 100 includes a metal ring 110 (also referred to herein as a "retaining member" or "insert element") adapted to be inserted into and held within a plate carrier. In another embodiment, the ring 110 is formed from another substantially rugged, non-deformable material, such as, for example, ceramic, plastic, fiberglass, or other composite material. Plate carriers are positioned within orifice fittings, which are installed at select locations along a pipeline for measuring and estimating properties within the pipeline, such as, for example, internal pressure and flow rate. Orifice fittings are typically designed to allow for easy and rapid insertion or removal of measuring devices into the pipeline P without interrupting the flow of fluid.

In at least one embodiment of the invention, the ring 110 is adapted to be held within a Daniel® plate carrier, available from Emerson Process Management®, Houston, Tex., United States. In one embodiment, the ring 110 has an outer circumference equal to the outer circumference of a Daniel® orifice plate (not shown). Daniel® orifice plates are custom fit to be held by the Daniel® plate carrier, which are then placed within an orifice fitting to measure flow rate within a pipeline.

For example, in one embodiment of the invention, the ring 110 has an outer circumference of 8.4370 inches, an inner circumference of 8.0300 inches, and a thickness (measured from the outer surface 112 to the inner surface 114 of the ring 110) of 0.2035 inches. In another embodiment, the ring 110 has an outer circumference of 6.0250 inches and an inner circumference of 6.4320 inches. In yet another embodiment, the ring 110 has an outer circumference of 4.4070 inches and an inner circumference of 4.0000.

In another embodiment of the invention, as illustrated in FIG. 3, the device 100 further includes one or more metal spacers 300 to secure the ring 110 within the plate carrier if the dimensions of the ring 110 are substantially smaller than that of the plate carrier. Thus, the spacer 300 (also referred to as a "sealing ring") ensures a tight fit between the ring 110 and the plate carrier. In another embodiment, the spacer is formed from another substantially rugged, non-deformable material, such as, for example, ceramic, plastic, fiberglass, or other composite material. In another embodiment, a single spacer is used that surrounds the entire outer surface 112 of the ring 110. In yet another embodiment, the spacers 300 have varying shapes and sizes, depending on the shapes and sizes of the ring 110 and plate carrier. In still another embodiment, the ring 110 has a non-circular shape, such as, for example, polygonal, rectangular, or oval-shaped.

The device 100 further includes a stainless steel metal hub 120 (also referred to herein as a "lug") connected to the inner surface 114 of the ring 110. In at least one embodiment, the hub 120 is attached to the ring 110 via tungsten inert gas (TIG) welding. The hub 120 is a pedestal, mounting, platform, or support that positions the measurement device C within the flow of fluid. As illustrated in FIG. 1, the hub 120 maintains the measurement device C off of the inner walls of the ring 110 and pipeline P while minimizing interference with the flow of fluid through the pipeline P.

In another embodiment, the hub 120 is formed from another material, such as, for example, ceramic, plastic, fiberglass, or other composite material. In yet another embodiment, the hub 120 is fastened to the ring 110 by an alternative means, such as, for example, bolts, screws, rivets, clamps, clasps, slot and tab engagements, and the like, or the hub 120 is integrally formed with the ring 110. In still another embodiment, the hub 120 has an alternative shape, such as, for example, a cylinder (e.g., rod, pole, shaft), a pyramid, or the hub 120 is pylon-shaped.

In at least one embodiment, the hub 120 has a general "block" shape and includes a bottom wall 121, a top wall 122, a front wall 123, a rear wall (not shown), a first side wall 125, and a second side wall 126. The bottom wall 121 is contoured such that the hub 120 rests on and can be easily welded to the inner surface 114 of the ring 110 so as to extend axially beyond the ring 110. More specifically, the bottom wall 121 has a ring-receiving notch, or ramp, 121A to adjust to the rounded contour of the ring 110. In one embodiment, the bottom wall 121 has a length (i.e., the distance from the first side wall 125 and the second side wall 126) of 0.6250 inches; and, the distance from the bottom wall 121 to the top wall 122 is 0.500 inches. In yet another embodiment, the bottom wall 121 has a convex curvature. In still another embodiment, the bottom wall 121 has a groove having a first end at the first side wall 125, and a second end at the second side wall 126. The groove is dimensioned to receive the ring 110 therein.

The top wall 122 has a shelf 122A adjacent the second side wall 126 for receiving a seat 130 thereon. Thus, the hub 120 has a generally L-shaped cross-section wherein the first side wall 125 is taller than the second side wall 126. In another embodiment, the shelf 122A is adjacent the first side wall 125, wherein the second side wall 126 is taller than the first side wall 125.

In at least one embodiment, the first side wall 125 and the second side wall 126 each form rectangular surfaces, wherein the first side wall 125 has a height to accommodate the thickness of the seat 130, described below, and the measuring device C. As illustrated, the first side wall 125 has a height of 0.2500 inches; and, the second side wall 126 has a height of 0.3100 inches. In another embodiment, the top wall 122 lacks the shelf 122A, wherein the seat 130 is a thin rectangular block that sits directly on the top wall 122.

In at least one embodiment of the invention, the shelf 122A of the hub 120 has a channel (threaded or un-threaded) for receiving a fastener 140 therein. As described more fully below, the fastener 140 secures the corrosion measurement device C to the device 100.

The seat 130 provides a dielectric insulation layer between the measurement device C and the hub 120. Thus, electric charges do not flow from the measurement device C to the device 100. In at least one embodiment, the seat 130 includes a bottom wall 131, a top wall 132, a front wall 133, a rear wall (not shown), a first side wall 135, and a second side wall 136. As illustrated in FIG. 4, the bottom wall 131 of the seat 130 is positioned on the shelf 122A of the hub 120. In one embodiment, the seat 130 is attached to the hub 120 via adhesive.

In at least one embodiment, the seat 130 has a length (i.e., the distance from the first side wall 135 and the second side wall 136) of 0.5625 inches. The top wall 132 of the seat 130 has a shelf 132A adjacent the second side wall 136 for receiving the measurement device C thereon. Thus, the L-shaped seat 130 preferably formed of rigid, non-deformable plastic (e.g., Derlin™) where the back of the L is twice the thickness of the main leg. In another embodiment, the shelf 132A is adjacent the first side wall 135, wherein the second side wall 136 is taller than the first side wall 135.

In another embodiment, the seat 130 lacks the shelf 132A, wherein the measurement device C sits directly on the top wall 132. In yet another embodiment, the seat 130 has an alternative shape, such as, for example, a rectangular block, a cylinder (e.g., rod, pole, shaft), a pyramid, or the seat 130 is pylon-shaped.

In at least one embodiment of the invention, the seat 130 and the measurement device C each have an aperture (threaded or unthreaded) for receiving the fastener 140 therein. More specifically, when the apertures of the seat 130 and the measurement device C are aligned with the channel of the hub 120, as illustrated in FIGS. 1 and 4, the fastener 140 is inserted into the aperture of the measurement device C, through the aperture of the seat 130, and into the channel of the hub 120. Thus, both the seat 130 and the measurement device C are removably secured to the hub 120 via the fastener 140.

In another embodiment, the seat 130 is permanently or removably secured to the hub 120 via other means, such as, for example, welding, adhesive, clamps, clasps, slot and tab engagements, and the like. In one embodiment, the hub 120 lacks a channel, wherein the fastener 140 does not extend into the hub 120. In such an embodiment, the fastener 140 engages a threaded aperture/channel in the seat 130. In another embodiment, the ring 110 also has a threaded channel for receiving the fastener 140 therein. In yet another embodiment, the measurement device C is secured to the device 100 via other means, such as, for example, clamps, clasps, slot and tab engagements, and the like.

In at least one embodiment of the invention, the measurement device C is a thin rectangular tablet or card having a thickness (distance from top wall to bottom wall) of 0.1250 inches, a length (distance from first side wall to second side wall) of 1.2500 inches, and a width (distance from front wall to rear wall) of 0.500 inches.

To estimate the degree of corrosion of the pipeline P, the measurement device C is placed inside of the plate carrier via the device 100. After a predetermined amount of time, the device 100 is removed from the plate carrier and the measurement device C is analyzed. By determining the degree of corrosion of the measurement device C, the degree of corrosion of the pipeline P is estimated.

In at least one embodiment of the invention, the fastener 140 is a ¼ inch nylon screw. In another embodiment, the fastener 140 is formed in varying shapes and sizes from another material, such as, for example, ceramic, plastic, fiberglass, or other composite and/or non-reactive material. In yet another embodiment, the fastener 140 is a bolt, rivet, dowel, clamp, clasp, slot and tab engagement, and the like.

FIG. 5 is a flow diagram of a method of forming an insert for an orifice fitting in a pipeline according to an embodiment of the invention. The orifice fitting includes a carrier, wherein the carrier has select cross-sectional interior dimensions corresponding to cross-sectional interior dimensions of the pipeline. A lug is positioned on an inner surface of a retaining member such that the lug projects inwardly from the inner surface of the retaining member towards a center of the retaining member (510). The retaining member has an exteriorly facing surface that dimensionally corresponds to the select cross-sectional interior dimensions of the carrier to positionally stabilize the insert in a predetermined position within the pipeline and in substantial registry with the orifice fitting.

A dielectric insulated layer is positioned on an inwardly facing surface of the lug (520). Thus, the lug is positioned such that the lug is between the retaining member and the dielectric insulated layer. The dielectric insulating layer includes a first element of a cooperating attachment member. The cooperating attachment member removably securely retains a corrosion coupon on the dielectric insulating layer upon engagement of the first element with a second element of the cooperating attachment member.

More specifically, in at least one embodiment, a corrosion coupon is positioned on an upper surface of the dielectric insulated layer (530). Thus, the dielectric insulated layer is positioned such that the dielectric insulated layer is between the lug and the corrosion coupon. Both the corrosion coupon and the dielectric insulated layer have a vertical aperture, such that when the apertures are aligned with a channel in the lug, a passage is formed for receiving the second element of the cooperating attachment member. For example, the second element is the elongated member of a screw; and, the channel in the lug is threaded. Thus, the corrosion coupon is securely fastened to the insert via the attachment member (540).

In at least one embodiment, the outer circumference of the retaining member is smaller than the opening in the carrier. Therefore, one or more spacers are positioned on the exteriorly facing surface of the retaining member (550). The spacers adjust the outer circumference of the insert such that the insert securely fits within the opening in the carrier.

Figure 6:
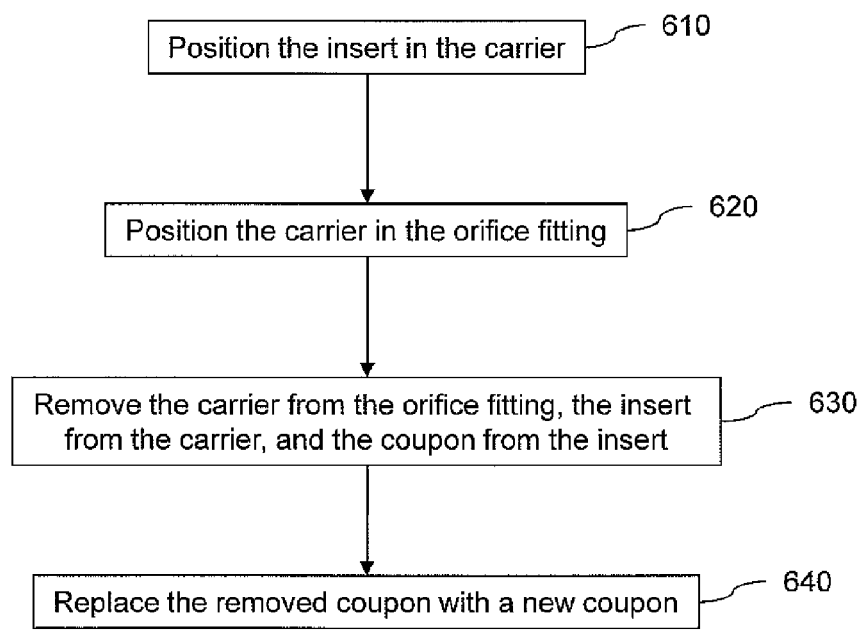
FIG. 6 is a flow diagram of a method of using an insert for an orifice fitting according to an embodiment of the invention.

FIG. 6 is a flow diagram of a method of using an insert for an orifice fitting in a pipeline according to an embodiment of the invention, wherein the orifice fitting includes a carrier and the insert includes a retaining member. The retaining member has an exteriorly facing surface dimensionally corresponding to the cross-sectional interior dimensions of the carrier.

The insert is positioned in the carrier such that the exteriorly facing surface of the retaining member engages an interiorly facing surface of the carrier (610). Thus, the insert is positionally stabilized in a predetermined position within the carrier. As described above, the insert includes a lug affixed to an interiorly facing surface of the retaining member, wherein the lug projects inwards towards the interior of the insert. The lug provides an interiorly facing mounting surface, upon which lies a dielectric insulating layer. A corrosion coupon is removably secured to the dielectric insulating layer with an attachment member (either before or after the insert is positioned within the carrier).

In at least one embodiment, one or more spacers are positioned on the exteriorly facing surface of the retaining member before the insert is positioned within the carrier. As described above, the spacer adjusts the outer circumference of the insert such that the insert securely fits within the opening in the carrier. Thus, an exteriorly facing surface of the spacer directly engages the interiorly facing surface of the carrier.

The carrier is positioned in the orifice fitting such that the corrosion coupon is securely fastened within the interior of the insert is positionally stabilized in a predetermined position within the interior of the pipeline (620). Accordingly, the corrosion coupon is exposed to the physical and chemical elements within the interior of the pipeline.

After a predetermined time period, the carrier is removed from the orifice fitting; the insert is removed from the carrier; and, the corrosion coupon is removed from the insert (630). The removed corrosion coupon is analyzed to estimate the degree of corrosion within the pipeline.

To conduct further testing within the pipeline, the removed corrosion coupon is replaced with a new corrosion coupon (640). More specifically, the new corrosion coupon is removably secured to the dielectric insulating layer of the insert with an attachment member. The insert, which includes the new corrosion coupon, is positioned in the carrier; and, the carrier is positioned in the orifice fitting.

Although specific example embodiments have been illustrated and described herein, those of ordinary skill in the art appreciate that other variations, aspects, or embodiments may be contemplated, and/or practiced without departing from the scope or the spirit of the appended claims.

The invention claimed is:

1. An insert for an orifice fitting in a pipeline, the orifice fitting including a carrier, the carrier having select cross-sectional interior dimensions corresponding to cross-sectional interior dimensions of the pipeline, said insert including:
   a retaining member having an exteriorly facing surface dimensionally corresponding to the select cross-sectional interior dimensions of the carrier to positionally stabilize said insert in a predetermined position within the pipeline and in substantial registry with the orifice fitting, said retaining member also having an interiorly facing surface;
   a lug affixed to said interiorly facing surface of said retaining member, said lug projecting inwards towards a center of said retaining member, said lug providing an interiorly facing mounting surface;
   a dielectric insulating layer on said interiorly facing mounting surface of said lug, said dielectric insulating layer including a first element of a cooperating attachment member; and
   a second element of said cooperating attachment member, said cooperating attachment member removably securely retains a corrosion coupon on said dielectric insulating layer upon engagement of said second element with said first element.

2. The insert according to claim 1, further including at least one spacer having an interiorly facing surface and an exteriorly facing surface, wherein said interiorly facing surface of said spacer engages said exteriorly facing surface of said retaining member, and wherein said exteriorly facing surface of said spacer engages an interiorly facing surface of the carrier.

3. The insert according to claim 1, wherein said lug is between said retaining member and said dielectric insulated layer.

4. The insert according to claim 1, wherein said dielectric insulated layer is between said lug and the corrosion coupon.

5. The insert according to claim 1, wherein said lug has an L-shape cross-section.

6. The insert according to claim 1, wherein said dielectric insulated layer has an L-shape cross-section.

7. The insert according to claim 1, wherein said first element of said cooperating attachment member includes one of an aperture and a threaded channel, and wherein said second element of said cooperating attachment member includes an elongated member of a screw.

8. The insert according to claim 7, wherein said screw is formed from non-reactive material.

9. The insert according to claim 1, wherein the coupon includes an aperture for receiving said second element of said cooperating attachment member.

10. The insert according to claim 1, wherein said lug includes a threaded channel for receiving said second element of said cooperating attachment member.

11. A device for retaining a coupon within a pipeline, said device including:
    an insert element having an outer surface and an inner surface;
    a hub projecting inwardly from said inner surface of said insert element towards a center of said insert element;
    a dielectric insulated seat having a bottom surface and a top surface, said bottom surface being connected to said hub; and
    a fastener for removably securing the coupon to said dielectric insulated seat.

12. The device according to claim 11, wherein said insert element is adapted to be removably secured within a plate carrier.

13. The device according to claim 12, further including at least one spacer between said insert element and the plate carrier.

14. The device according to claim 12, wherein the plate carrier is positioned within an orifice fitting located between two pipes of the pipeline.

15. The device according to claim 11, wherein said insert element is a ring.

16. A method of using an insert for an orifice fitting in a pipeline, the orifice fitting including a carrier, said method including:
    positioning the insert in the carrier such that an exteriorly facing surface of a retaining member of the insert engages an interiorly facing surface of the carrier to positionally stabilize the insert in a predetermined position within the carrier;
    positioning the carrier in the orifice fitting such that a corrosion coupon is securely fastened within an interior of the insert is positionally stabilized in a predetermined position within an interior of the pipeline, the corrosion coupon being removably secured on a dielectric insulating layer on a lug of the insert, the lug being affixed to an interiorly facing surface of the retaining member and projecting inwards towards the interior of the insert.

17. The method according to claim 16, further including removably securing the corrosion coupon to the dielectric insulating layer with an attachment member.

18. The method according to claim 16, further including:
    removing the carrier from the orifice fitting;
    removing the insert from the carrier; and
    removing the corrosion coupon from the insert.

19. The method according to claim 18, further including:
    replacing the removed corrosion coupon with a new corrosion coupon by removably securing the new corrosion coupon to the dielectric insulating layer of the insert with an attachment member;
    positioning the insert including the new corrosion coupon in the carrier; and
    positioning the carrier in the orifice fitting.

20. The method according to claim 16, further including positioning at least one spacer on the exteriorly facing surface of the retaining member, wherein said positioning of the insert in the carrier includes positioning the insert such that an exteriorly facing surface of the spacer directly engages the interiorly facing surface of the carrier.

* * * * *